United States Patent
Gokharu

(10) Patent No.: US 10,159,491 B2
(45) Date of Patent: Dec. 25, 2018

(54) ENDOSCOPIC REPOSABLE SURGICAL CLIP APPLIER

(71) Applicant: Covidien LP, Mansfield, MA (US)

(72) Inventor: Rajkumar Gokharu, Andhra Pradesh (IN)

(73) Assignee: Covidien LP, Mansfield, MA (US)

( * ) Notice: Subject to any disclaimer, the term of this patent is extended or adjusted under 35 U.S.C. 154(b) by 477 days.

(21) Appl. No.: 15/001,633

(22) Filed: Jan. 20, 2016

(65) Prior Publication Data

US 2016/0262764 A1    Sep. 15, 2016

Related U.S. Application Data

(60) Provisional application No. 62/130,724, filed on Mar. 10, 2015.

(51) Int. Cl.
| | |
|---|---|
| *A61B 17/10* | (2006.01) |
| *A61B 17/128* | (2006.01) |
| *A61B 17/122* | (2006.01) |
| *A61B 17/00* | (2006.01) |
| *A61B 17/29* | (2006.01) |
| *A61B 17/12* | (2006.01) |

(52) U.S. Cl.
CPC ........ *A61B 17/1285* (2013.01); *A61B 17/105* (2013.01); *A61B 17/1222* (2013.01); *A61B 2017/0046* (2013.01); *A61B 2017/12004* (2013.01); *A61B 2017/2922* (2013.01)

(58) Field of Classification Search
CPC ....... A61B 17/10; A61B 17/105; A61B 17/12; A61B 17/128; A61B 17/1285; A61B 17/068; A61B 17/0682; A61B 2017/12004; A61B 2017/0046; A61B 2017/2922

USPC .................................. 606/142, 143
See application file for complete search history.

(56) References Cited

U.S. PATENT DOCUMENTS

| | | |
|---|---|---|
| 3,120,230 A | 2/1964 | Skold |
| 3,363,628 A | 1/1968 | Wood |
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,242,902 A | 1/1981 | Green |

(Continued)

FOREIGN PATENT DOCUMENTS

| | | |
|---|---|---|
| AU | 2010200641 A1 | 10/2010 |
| CN | 1939231 A | 4/2007 |

(Continued)

OTHER PUBLICATIONS

Chinese First Office Action corresponding to Chinese Appln. No. CN 201410076318.8 dated Jan. 23, 2017.

(Continued)

*Primary Examiner* — Melanie Tyson

(57) ABSTRACT

A surgical clip applier is provided and includes a handle assembly and an endoscopic assembly selectively connectable to a housing of the handle assembly. The handle assembly includes a housing, a trigger pivotally supported on and extending from the housing, and a drive assembly supported within the housing and operatively actuatable by the trigger. The endoscopic assembly includes a shaft assembly extending from the housing, the shaft assembly including an outer tube and a pair of jaws supported in and extending from a distal end of the outer tube.

22 Claims, 6 Drawing Sheets

(56) References Cited

U.S. PATENT DOCUMENTS

| | | |
|---|---|---|
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |

(56) References Cited

U.S. PATENT DOCUMENTS

| | | |
|---|---|---|
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |

(56) References Cited

U.S. PATENT DOCUMENTS

| | | |
|---|---|---|
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,510,562 B2 | 3/2009 | Lindsay |
| 7,552,853 B2 | 6/2009 | Mas et al. |
| 7,637,917 B2 | 12/2009 | Whitfield et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,248 B2 | 6/2010 | Smith et al. |
| 7,731,724 B2 | 6/2010 | Huitema et al. |
| 7,740,641 B2 | 6/2010 | Huitema |
| 7,752,853 B2 | 7/2010 | Singh et al. |
| 7,753,250 B2 | 7/2010 | Clauson et al. |
| 7,766,207 B2 | 8/2010 | Mather et al. |
| 7,819,886 B2 | 10/2010 | Whitfield et al. |
| 7,887,553 B2 | 2/2011 | Lehman et al. |
| 7,905,890 B2 | 3/2011 | Whitfield et al. |
| 7,942,885 B2 | 5/2011 | Sixto, Jr. et al. |
| 7,963,433 B2 | 6/2011 | Whitman et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,142,451 B2 | 3/2012 | Boulnois et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,187,290 B2 | 5/2012 | Buckman et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,308,743 B2 | 11/2012 | Matsuno et al. |
| 8,328,822 B2 | 12/2012 | Huitema et al. |

(56) References Cited

U.S. PATENT DOCUMENTS

| | | |
|---|---|---|
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,717 B2 | 11/2013 | Sorrentino et al. |
| 8,603,109 B2 | 12/2013 | Aranyi et al. |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,213 B2 | 4/2014 | Shelton, IV et al. |
| 8,709,027 B2 | 4/2014 | Adams et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,920,438 B2 | 12/2014 | Aranyi et al. |
| 8,950,646 B2 | 2/2015 | Viola |
| 8,961,542 B2 | 2/2015 | Whitfield et al. |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 9,011,464 B2 | 4/2015 | Zammataro |
| 9,011,465 B2 | 4/2015 | Whitfield et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,186,136 B2 | 11/2015 | Malkowski et al. |
| 9,186,153 B2 | 11/2015 | Zammataro |
| 9,220,507 B1 | 12/2015 | Patel et al. |
| 9,358,011 B2 | 6/2016 | Sorrentino et al. |
| 9,358,015 B2 | 6/2016 | Sorrentino et al. |
| 9,364,216 B2 | 6/2016 | Rockrohr et al. |
| 9,364,239 B2 | 6/2016 | Malkowski |
| 9,364,240 B2 | 6/2016 | Whitfield et al. |
| 9,393,024 B2 | 7/2016 | Whitfield et al. |
| 9,398,917 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,498,227 B2 | 11/2016 | Zergiebel et al. |
| 9,526,501 B2 | 12/2016 | Malkowski |
| 9,545,254 B2 | 1/2017 | Sorrentino et al. |
| 9,642,627 B2 | 5/2017 | Zammataro |
| 9,687,247 B2 | 6/2017 | Kranyi et al. |
| 9,717,505 B2 | 8/2017 | Whitfield et al. |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,775,623 B2 | 10/2017 | Zammataro et al. |
| 9,775,624 B2 | 10/2017 | Rockrohr et al. |
| 9,848,886 B2 | 12/2017 | Malkowski et al. |
| 9,855,043 B2 | 1/2018 | Malkowski |
| 9,931,124 B2 | 4/2018 | Gokharu |
| 9,968,361 B2 | 5/2018 | Aranyi et al. |
| 9,968,362 B2 | 5/2018 | Malkowski et al. |
| 2001/0047178 A1 | 11/2001 | Peters |
| 2002/0040226 A1 | 4/2002 | Laufer et al. |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2003/0014060 A1 | 1/2003 | Wilson et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake |
| 2003/0167063 A1 | 9/2003 | Kerr |
| 2003/0208231 A1 | 11/2003 | Williamson et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2005/0010242 A1 | 1/2005 | Lindsay |
| 2005/0080440 A1 | 4/2005 | Durgin et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |

(56) References Cited

U.S. PATENT DOCUMENTS

| | | |
|---|---|---|
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0212050 A1 | 9/2006 | D'Agostino et al. |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0066981 A1 | 3/2007 | Meagher |
| 2007/0073314 A1 | 3/2007 | Gadberry et al. |
| 2007/0083218 A1 | 4/2007 | A. Morris |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0173866 A1 | 7/2007 | Sorrentino et al. |
| 2007/0175949 A1 | 8/2007 | Shelton et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0083813 A1 | 4/2008 | Zemlok et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0167671 A1 | 7/2008 | Giordano et al. |
| 2008/0228199 A1 | 9/2008 | Cropper et al. |
| 2008/0243145 A1 | 10/2008 | Whitfield et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0312670 A1 | 12/2008 | Lutze et al. |
| 2008/0319456 A1 | 12/2008 | Hart |
| 2009/0076533 A1 | 3/2009 | Kayan et al. |
| 2009/0088777 A1 | 4/2009 | Miyagi et al. |
| 2009/0088783 A1 | 4/2009 | Kennedy et al. |
| 2009/0171380 A1 | 7/2009 | Whiting |
| 2009/0182193 A1 | 7/2009 | Whitman et al. |
| 2009/0209946 A1 | 8/2009 | Swayze et al. |
| 2009/0222003 A1 | 9/2009 | Otley |
| 2009/0228023 A1 | 9/2009 | Cui |
| 2009/0228024 A1 | 9/2009 | Whitfield et al. |
| 2009/0264904 A1 | 10/2009 | Aldrich et al. |
| 2009/0299382 A1 | 12/2009 | Zergiebel |

(56) References Cited

U.S. PATENT DOCUMENTS

| | | |
|---|---|---|
| 2009/0326558 A1 | 12/2009 | Cui et al. |
| 2010/0049216 A1 | 2/2010 | Zergiebel |
| 2010/0057105 A1 | 3/2010 | Sorrentino et al. |
| 2010/0057107 A1 | 3/2010 | Sorrentino et al. |
| 2010/0069935 A1 | 3/2010 | Crainich |
| 2010/0274262 A1 | 10/2010 | Schulz et al. |
| 2010/0274264 A1 | 10/2010 | Schulz et al. |
| 2011/0054498 A1 | 3/2011 | Monassevitch et al. |
| 2011/0082474 A1 | 4/2011 | Bindra et al. |
| 2011/0087241 A1 | 4/2011 | Nguyen |
| 2011/0087243 A1 | 4/2011 | Nguyen et al. |
| 2011/0112552 A1 | 5/2011 | Lehman et al. |
| 2011/0137323 A1 | 6/2011 | Malkowski et al. |
| 2011/0137324 A1 | 6/2011 | Boudreaux et al. |
| 2011/0144662 A1 | 6/2011 | McLawhorn et al. |
| 2011/0144665 A1 | 6/2011 | Malkowski |
| 2011/0190791 A1 | 8/2011 | Jacobs et al. |
| 2011/0208211 A1 | 8/2011 | Whitfield et al. |
| 2011/0208212 A1 | 8/2011 | Zergiebel et al. |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |
| 2011/0230900 A1 | 9/2011 | Sarradon |
| 2011/0245847 A1 | 10/2011 | Menn et al. |
| 2011/0245848 A1 | 10/2011 | Rosenberg et al. |
| 2011/0251608 A1 | 10/2011 | Timm et al. |
| 2011/0295290 A1 | 12/2011 | Whitfield |
| 2011/0313437 A1 | 12/2011 | Yeh |
| 2012/0029534 A1 | 2/2012 | Whitfield et al. |
| 2012/0041455 A1 | 2/2012 | Martinez |
| 2012/0046671 A1 | 2/2012 | Matsuoka et al. |
| 2012/0048759 A1 | 3/2012 | Disch et al. |
| 2012/0059394 A1 | 3/2012 | Brenner et al. |
| 2012/0065647 A1 | 3/2012 | Litscher et al. |
| 2012/0109158 A1 | 5/2012 | Zammataro |
| 2012/0116420 A1 | 5/2012 | Sorrentino et al. |
| 2012/0197269 A1 | 8/2012 | Zammataro |
| 2012/0265220 A1 | 10/2012 | Menn |
| 2012/0277765 A1 | 11/2012 | Zammataro et al. |
| 2012/0330326 A1 | 12/2012 | Creston et al. |
| 2013/0110135 A1 | 5/2013 | Whitfield et al. |
| 2013/0131697 A1 | 5/2013 | Hartoumbekis |
| 2013/0165951 A1 | 6/2013 | Blake, III |
| 2013/0165952 A1 | 6/2013 | Whitfield et al. |
| 2013/0172909 A1 | 7/2013 | Harris |
| 2013/0172910 A1 | 7/2013 | Malkowski |
| 2013/0172911 A1 | 7/2013 | Rockrohr et al. |
| 2013/0172912 A1 | 7/2013 | Whitfield et al. |
| 2013/0253541 A1 | 9/2013 | Zergiebel |
| 2013/0274767 A1 | 10/2013 | Sorrentino et al. |
| 2013/0289583 A1 | 10/2013 | Zergiebel et al. |
| 2013/0296891 A1 | 11/2013 | Hartoumbekis |
| 2013/0296892 A1 | 11/2013 | Sorrentino et al. |
| 2013/0310849 A1 | 11/2013 | Malkowski |
| 2013/0325040 A1 | 12/2013 | Zammataro |
| 2014/0005693 A1 | 1/2014 | Shelton, IV et al. |
| 2014/0039526 A1 | 2/2014 | Malkowski |
| 2014/0052157 A1 | 2/2014 | Whitfield et al. |
| 2014/0058412 A1 | 2/2014 | Aranyi et al. |
| 2014/0194903 A1 | 7/2014 | Malkowski et al. |
| 2014/0207156 A1 | 7/2014 | Malkowski |
| 2014/0263565 A1 | 9/2014 | Lytle, IV et al. |
| 2014/0316441 A1 | 10/2014 | Zergiebel et al. |
| 2014/0330291 A1 | 11/2014 | Whitfield et al. |
| 2015/0005790 A1 | 1/2015 | Whitfield et al. |
| 2015/0032131 A1 | 1/2015 | Sorrentino et al. |
| 2015/0045816 A1 | 2/2015 | Aranyi et al. |
| 2015/0066057 A1 | 3/2015 | Rockrohr et al. |
| 2015/0080916 A1 | 3/2015 | Aranyi et al. |
| 2015/0127022 A1 | 5/2015 | Whitfield et al. |
| 2015/0164511 A1 | 6/2015 | Whitfield et al. |
| 2015/0190138 A1 | 7/2015 | Whitfield et al. |
| 2015/0190139 A1 | 7/2015 | Zammataro |
| 2015/0282808 A1 | 10/2015 | Sorrentino et al. |
| 2015/0351771 A1 | 12/2015 | Malkowski et al. |
| 2015/0351772 A1 | 12/2015 | Malkowski et al. |
| 2016/0030044 A1 | 2/2016 | Zammataro |
| 2016/0030045 A1 | 2/2016 | Malkowski et al. |
| 2016/0113655 A1 | 4/2016 | Holsten |
| 2016/0151071 A1 | 6/2016 | Tokarz et al. |
| 2016/0192940 A1 | 7/2016 | Gokharu |
| 2016/0213377 A1 | 7/2016 | Shankarsetty |
| 2016/0242767 A1 | 8/2016 | Kasvikis |
| 2016/0262764 A1 | 9/2016 | Gokharu |
| 2017/0128071 A1 | 5/2017 | Holsten et al. |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |

FOREIGN PATENT DOCUMENTS

| | | |
|---|---|---|
| CN | 1994236 A | 7/2007 |
| CN | 101530340 A | 9/2009 |
| CN | 101658437 A | 3/2010 |
| CN | 101664329 A | 3/2010 |
| CN | 101664331 A | 3/2010 |
| CN | 201683954 U | 12/2010 |
| CN | 103083059 A | 5/2013 |
| CN | 103181809 A | 7/2013 |
| CN | 103181810 A | 7/2013 |
| CN | 104487006 A | 4/2015 |
| DE | 20 2005 001664 U1 | 5/2005 |
| DE | 20 2009 006113 U1 | 7/2009 |
| EP | 0000756 A1 | 2/1979 |
| EP | 0 073 655 A1 | 3/1983 |
| EP | 0 085 931 A2 | 8/1983 |
| EP | 0 086 721 A2 | 8/1983 |
| EP | 0 089 737 A1 | 9/1983 |
| EP | 0 092 300 A1 | 10/1983 |
| EP | 0 324 166 A2 | 7/1989 |
| EP | 0 392 750 A1 | 10/1990 |
| EP | 0 406 724 A1 | 1/1991 |
| EP | 0 409 569 A1 | 1/1991 |
| EP | 0514139 A3 | 3/1993 |
| EP | 0 569 223 A1 | 11/1993 |
| EP | 0 594 003 A1 | 4/1994 |
| EP | 0 598 529 A2 | 5/1994 |
| EP | 0 622 049 A1 | 11/1994 |
| EP | 0 685 204 A1 | 12/1995 |
| EP | 0 732 078 A2 | 9/1996 |
| EP | 0 755 655 A2 | 1/1997 |
| EP | 0 760 230 A1 | 3/1997 |
| EP | 0 769 274 A1 | 4/1997 |
| EP | 0 769 275 A1 | 4/1997 |
| EP | 0 834 286 A1 | 4/1998 |
| EP | 1 317 906 A1 | 6/2003 |
| EP | 1 609 427 A1 | 12/2005 |
| EP | 1 712 187 A2 | 10/2006 |
| EP | 1 712 191 A2 | 10/2006 |
| EP | 1 757 236 A2 | 2/2007 |
| EP | 1 813 199 A1 | 8/2007 |
| EP | 1 894 531 A2 | 3/2008 |
| EP | 1 908 423 A2 | 4/2008 |
| EP | 1 913 881 A1 | 4/2008 |
| EP | 2 229 895 A1 | 9/2010 |
| EP | 2 332 471 A1 | 6/2011 |
| EP | 2 412 318 A2 | 2/2012 |

(56) References Cited

FOREIGN PATENT DOCUMENTS

| | | |
|---|---|---|
| EP | 2 412 319 A2 | 2/2012 |
| EP | 2 752 165 A2 | 7/2014 |
| GB | 2073022 A | 10/1981 |
| GB | 2 132 899 A | 7/1984 |
| JP | 2003-033361 A | 2/2003 |
| JP | 2006-154230 A | 6/2006 |
| JP | 2006-277221 A | 10/2006 |
| JP | 2008-017876 A | 1/2008 |
| JP | 2008-515550 A | 5/2008 |
| JP | 2009-198991 A | 9/2009 |
| WO | 95/34246 A1 | 12/1995 |
| WO | 01/65997 A2 | 9/2001 |
| WO | 2001-66001 A2 | 9/2001 |
| WO | 2001-67965 A1 | 9/2001 |
| WO | 2003-086207 A1 | 10/2003 |
| WO | 2003-092473 A2 | 11/2003 |
| WO | 2004-032762 A1 | 4/2004 |
| WO | 2005-091457 A1 | 9/2005 |
| WO | 2006-042076 A2 | 4/2006 |
| WO | 2006-042084 A2 | 4/2006 |
| WO | 2006-042110 A2 | 4/2006 |
| WO | 2006-042141 A2 | 4/2006 |
| WO | 2006-135479 A2 | 12/2006 |
| WO | 2008-118928 A2 | 10/2008 |
| WO | 2008/127968 A2 | 10/2008 |
| WO | 2013-040378 A1 | 3/2013 |

OTHER PUBLICATIONS

Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 34475 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Extended European Search Report corresponding to counterpart Int'l Appln. No. EP 16 15 9324.9, dated May 20, 2016.
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).

The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).

(56) References Cited

OTHER PUBLICATIONS

The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
Chinese First Office Action corresponding to counterpart Int'l Appln. No. CN 201210586826.1 dated Dec. 30, 2015.
Extended European Search Report corresponding to counterpart Int'l Appln. No. EP 15 19 1313.4 dated Feb. 1, 2016.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
International Search Report & Written Opinion corresponding to Int'l Appln. No. PCT/CN2015/091603 dated Jul. 8, 2016.
European Office Action corresponding to EP 12 152 989.5 dated May 4, 2015.
Australian Office Action corresponding to AU 2009212759 dated May 7, 2015.
Chinese Office Action corresponding to counterpart Int'l Appln. No. CN 201210212642.9 dated Jun. 3, 2015.
European Office Action corresponding to counterpart Int'l Appln. No. 04 719 757.9 dated Jun. 12, 2015.
European Office Action corresponding to counterpart Int'l Appln. No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Extended European Search Report corresponding to counterpart Int'l Application No. EP 14 19 2026.4 dated Jul. 17, 2015.
Japanese Office Action corresponding to counterpart Int'l Application No. JP 2011-160126 dated Aug. 10, 2015.
Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 1, 2015.
Extended European Search Report corresponding to counterpart Int'l Application No. EP 11 25 0674.6 dated Oct. 1, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart Int'l Application No. EP 15 17 3809.3 dated Nov. 25, 2015.
Chinese Office Action corresponding to counterpart Int'l Application No. CN 201210586814.9 dated Dec. 2, 2015.
Extended European Search Report corresponding to counterpart Int'l Application No. EP 12 17 2940.4 dated Dec. 14, 2015.

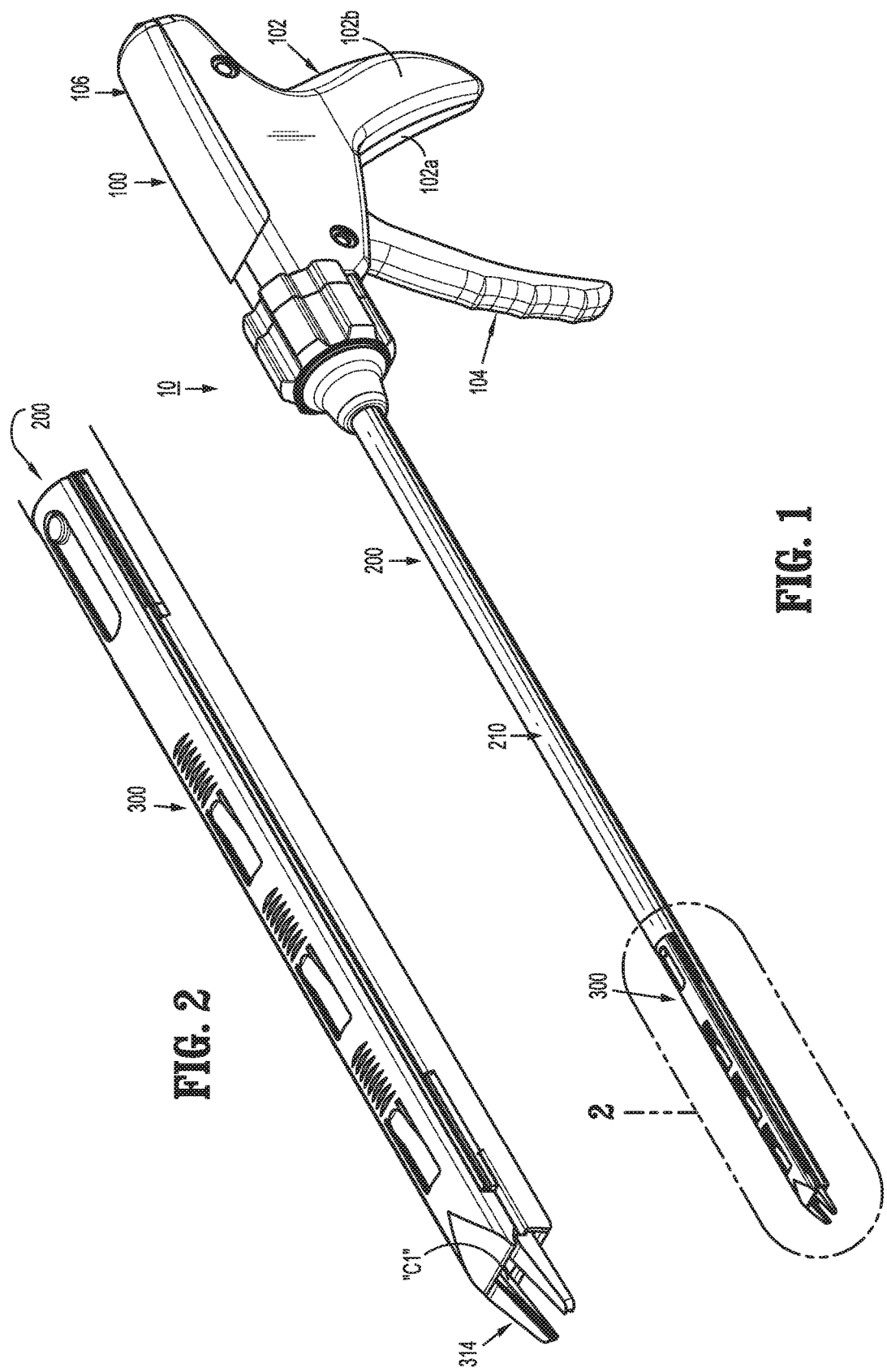

ENDOSCOPIC REPOSABLE SURGICAL CLIP APPLIER

CROSS-REFERENCE TO RELATED APPLICATIONS

This application claims the benefit of and priority to U.S. Provisional Patent Application No. 62/130,724 filed Mar. 10, 2015, the entire disclosure of which is incorporated by reference herein.

BACKGROUND

Technical Field

The present disclosure relates to surgical clip appliers. More particularly, the present disclosure relates to endoscopic reposable surgical clip appliers having a reusable handle assembly, a reusable shaft assembly, and a disposable clip cartridge assembly.

Description of Related Art

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip during an entry to the body cavity. Such clips are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 by Pratt et al., the contents of which is also hereby incorporated by reference herein in its entirety. These devices are typically, though not necessarily, used during a single surgical procedure. U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine so as to advance and form multiple clips during a single entry into a body cavity.

During endoscopic or laparoscopic procedures it may be desirable and/or necessary to use different size surgical clips depending on the underlying tissue or vessels to be ligated. In order to reduce overall costs of a surgical clip applier, it is desirable for a single surgical clip applier to be loadable with and capable of firing different size surgical clips as needed.

Accordingly, a need exists for endoscopic surgical clip appliers that include reusable handle assemblies, reusable shaft assemblies, and disposable clip cartridge assemblies, with each clip cartridge assembly being loaded with a particularly sized clip (e.g., small, medium, or large).

SUMMARY

According to an aspect of the present disclosure, a surgical clip applier is provided and includes a handle assembly and an endoscopic assembly selectively connectable to a housing of the handle assembly. The handle assembly includes a housing; a trigger pivotally supported on and extending from the housing; and a drive assembly supported within the housing and operatively actuatable by the trigger. The drive assembly includes at least one linkage connected to the trigger, the at least one linkage slidably supported in the housing; a guide block slidably supported in the housing, the guide block operatively connected to the trigger; a clip pusher bar slidably supported in the guide block, the clip pusher bar including a flange at a proximal end thereof; a toggle supported in the housing and located distal of the flange of the clip pusher bar, the toggle actuatable between a first position and a second position, wherein the toggle is configured to limit the distal translation of the clip pusher bar when the toggle is in the first position; and a push rod supported in the housing, the push rod engageable by the at least one linkage to actuate the toggle between the first position and the second position. The endoscopic assembly includes a shaft assembly extending from the housing, the shaft assembly including an outer tube; and a pair of jaws supported in and extending from a distal end of the outer tube, wherein when the toggle of the handle assembly in the second position, the pair of jaws are free to form a surgical clip on tissue.

The at least one linkage may include a first end and a second end, the first end of the linkage being pivotably connected to the trigger and the second end of the linkage being pivotably connected to the guide block such that actuation of the trigger translates the guide block proximally.

The first end of the at least one linkage and the trigger may be slidably coupled to a slot defined in the housing such that upon actuation of the trigger, the first end of the at least one linkage rides along the slot.

In use, as the first end of the at least one linkage rides along the slot, the at least one linkage may exert a force on the push rod such that the push rod translates proximally to exert a force on the toggle to actuate the toggle from the first position to the second position.

The toggle may be spring loaded and may include a bias such that the toggle abuts the flange in the first position.

In use, in the second position, there may be a clearance between the toggle and the flange such that the clip pusher bar is able to translate distally to locate the flange distal to the toggle.

The drive assembly may further include a biasing member acting on the clip pusher bar to urge the clip pusher bar in a distal direction.

In use, a force exerted by the bias of the toggle may be greater than a force exerted by the biasing member acting on the clip pusher bar such that the biasing member is unable to push the flange past the toggle when the toggle is in the first position.

The drive assembly may further include a trigger return spring acting on the trigger to urge the trigger to an unactuated position.

In use, in the second position, the biasing member may act on the clip pusher bar to urge the clip pusher bar distally until the flange thereof abuts the guide block.

In use, when the trigger is actuated, the at least one linkage may simultaneously engage the push rod and the guide block such that the toggle is in the second position and the guide block drives the abutting flange proximally past the toggle.

According to another aspect of the present disclosure, a surgical clip applier is provided and includes a handle assembly and an endoscopic assembly selectively connectable to a housing of the handle assembly. The handle assembly includes a housing; a trigger pivotally supported on and extending from the housing; and a drive assembly supported within the housing and operatively actuatable by the trigger. The drive assembly includes a distal linkage slidably supported in the housing, the distal linkage including a first end and a second end, the second end of the distal linkage connected to the trigger; a proximal linkage slidably supported in the housing, the proximal linkage including a first end and a second end, the first end of the proximal linkage connected to the trigger; a jaw pusher slidably supported in the housing, the jaw pusher operatively connected to the trigger; a guide block slidably supported in the housing, the guide block operatively connected to the trigger; a clip pusher bar slidably supported in the guide block, the clip pusher bar including a flange at a proximal end thereof; a toggle supported in the housing and located distal of the flange of the clip pusher bar, the toggle actuatable between a first position and a second position, wherein the toggle is configured to limit the distal translation of the clip pusher bar when the toggle is in the first position; and a push rod supported in the housing, the push rod engageable by at least one of the proximal linkage and the distal linkage to actuate the toggle between the first position and the second position.

The endoscopic assembly includes a shaft assembly extending from the housing, the shaft assembly including an outer tube; and a pair of jaws supported in and extending from a distal end of the outer tube, wherein when the toggle of the handle assembly is in the second position, the pair of jaws are free to form a surgical clip on tissue.

In some embodiments, the distal linkage, the proximal linkage, and the trigger are slidably coupled to a slot defined in the housing such that upon actuation of the trigger, the distal linkage, the proximal linkage, and the trigger ride along a channel defined within the slot.

In use, actuation of the trigger may translate the jaw pusher distally and translates the guide block proximally.

In use, as the proximal linkage rides along the slot, the proximal linkage may exert a force on the push rod such that the push rod translates proximally to exert a force on the toggle to actuate the toggle from the first position to the second position.

According to another aspect of the present disclosure, a drive mechanism for a surgical clip applier is provided and includes a clip pusher bar and a toggle. The clip pusher bar includes a flange at a proximal end thereof and is configured for distal translation to advance a surgical clip.

In some embodiments, the drive mechanism further includes a linkage and a push rod engageable by the linkage to actuate the toggle between the first position and the second position.

The drive mechanism may further include a housing. The clip pusher bar, toggle, linkage, and push rod may all be positioned within the housing.

The drive mechanism may further include a trigger pivotally supported on and extending from the housing, and with the linkage connected to the trigger.

BRIEF DESCRIPTION OF THE DRAWINGS

A particular embodiment of a surgical clip applier is disclosed herein with reference to the drawings wherein:

FIG. 1 is a perspective view of a reposable endoscopic surgical clip applier, according to the present disclosure;

FIG. 2 is an enlarged view of the indicated area of detail of FIG. 1;

DETAILED DESCRIPTION OF EMBODIMENTS

Figure 3:
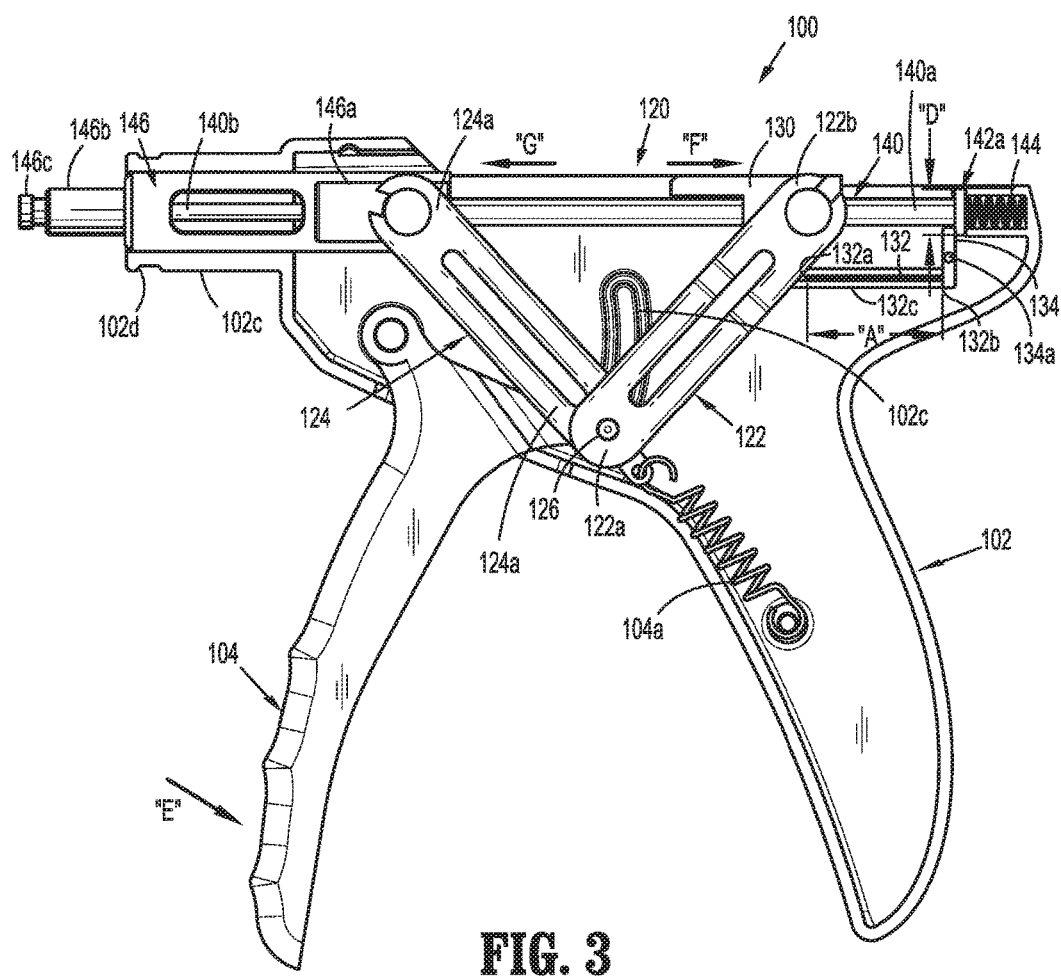
FIG. 3 is a side, elevational view of a handle assembly of the surgical clip applier of FIG. 1, with a housing half-section removed therefrom.

Embodiments of reposable endoscopic surgical clip appliers, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to FIGS. 1-6, an endoscopic surgical clip applier in accordance with an embodiment of the present disclosure is generally designated as 10. Surgical clip applier 10 generally includes a handle assembly 100, an endoscopic assembly 200 including a shaft assembly 210 extending distally from handle assembly 100; and at least one surgical clip cartridge assembly 300 selectively loadable into shaft assembly 210 of endoscopic assembly 200. In embodiments, it is contemplated that shaft 210 may be integrally formed with handle assembly 100. In alternative embodiments, it is contemplated that shaft 210 may be selectively connectable to handle assembly 100.

Briefly, shaft assembly 210 of endoscopic assembly 200 may have various outer diameters such as, for example, about 5 mm or about 10 mm, depending on intended use. Further, shaft assembly 210 may have various relatively elongated or shortened lengths depending on intended use, such as, for example, in bariatric surgery. In one embodiment, in bariatric surgery, shaft assembly 210 may have a length of between about 30 cm and about 40 cm. However one skilled in the art should appreciate that shaft assembly 210 may have any suitable length and the present disclosure is not limited to any of the above identified lengths.

Figure 6:
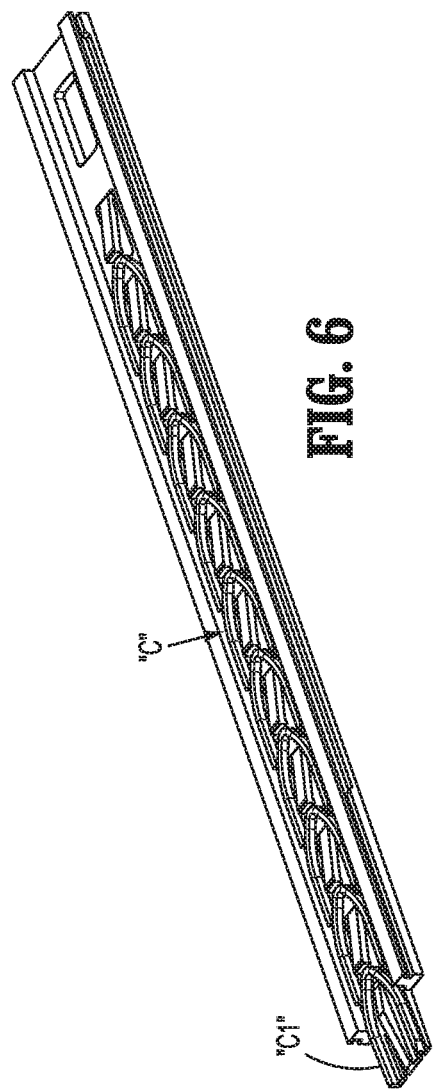
FIG. 6 is a perspective view of the clip cartridge tray of the surgical clip applier illustrating the plurality of surgical clips loaded therein.

In accordance with the present disclosure, each surgical clip cartridge assembly 300 may be loaded with a plurality of surgical clips "C" (see FIG. 6). The plurality of surgical clips "C" may be particularly sized (e.g., small surgical clips, medium surgical clips, or large surgical clips). Each surgical clip cartridge assembly 300 is configured to be selectively loaded into shaft assembly 210 of endoscopic assembly 200, and to be actuated by handle assembly 100 to fire and form the plurality of surgical clips "C" loaded therein onto underlying tissue and/or vessels "V" (see FIG. 7).

Referring now to FIGS. 1 and 3, handle assembly 100 of surgical clip applier 10 is shown. Handle assembly 100 includes a housing 102 having a first or right side half-section 102a and a second or left side half-section 102b. Handle assembly 100 includes a trigger 104 pivotally supported between right side half-section 102a and left side half-section 102b of housing 102. Trigger 104 is biased by a trigger return spring 104a (e.g., a spring) to an unactuated condition.

Housing 102 of handle assembly 100 may be formed of a suitable plastic or thermoplastic material. Handle assembly 100 includes a removable cover 106 or the like which provides access to a drive assembly 120 of clip applier 10. Housing 102 of handle assembly 100 further includes, as seen in FIG. 3, a nose 102c defining an annular flange 102d.

Figure 4:
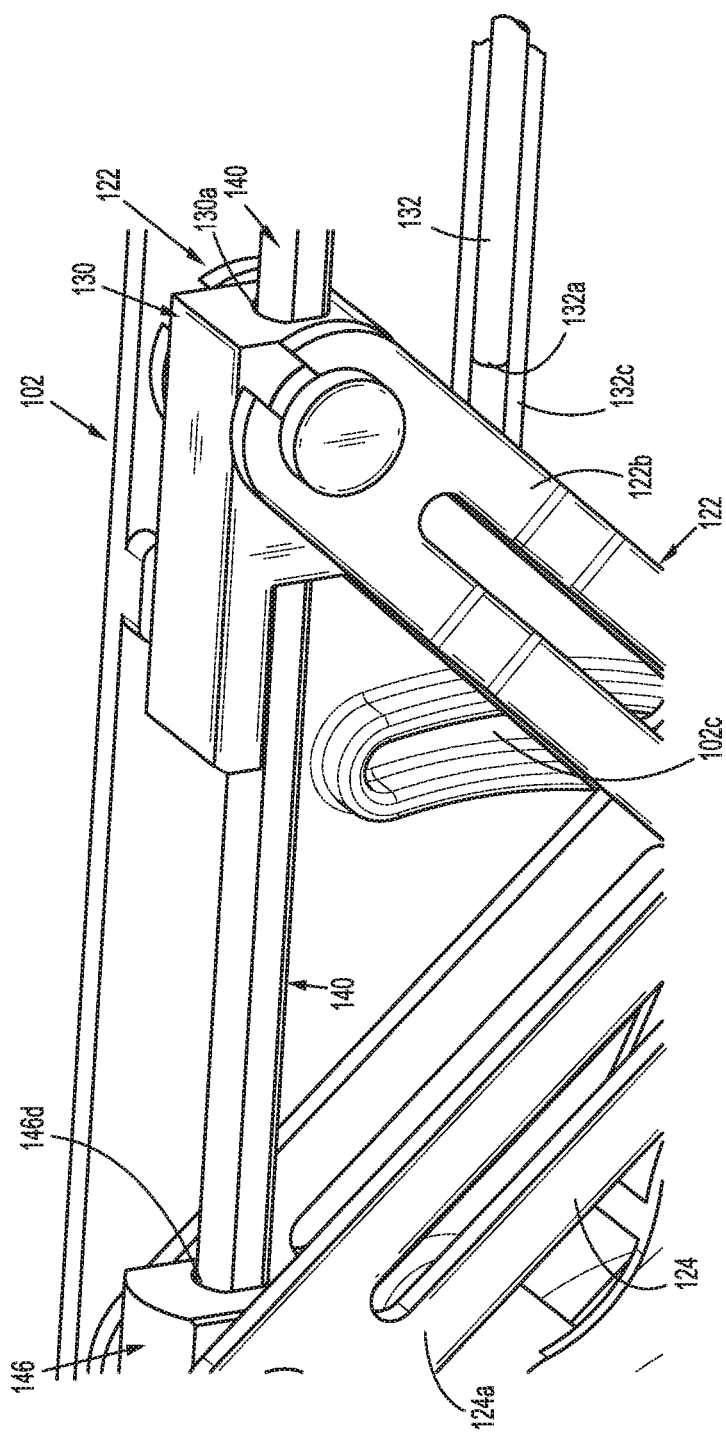
FIG. 4 is an enlarged, perspective view of a drive assembly of the handle assembly of FIG. 3.

Handle assembly 100 includes a drive assembly 120 operatively connected to trigger 104. Specifically, drive assembly 120 includes a proximal linkage 122, and a distal linkage 124. Though it is not shown in the figures, it is contemplated that in some embodiments, there may be a pair of proximal linkages 122 and a pair of distal linkages 124. Proximal linkage 122 includes a distal coupling portion 122a pivotally connected to trigger 104, and a proximal coupling portion 122b pivotally connected to a guide block 130. As shown in FIG. 4, guide block 130 defines a longitudinally extending passage 130a therethrough.

Distal linkage 124 includes a distal coupling portion 124a pivotally connected to a jaw pusher 146, and a proximal coupling portion 124b pivotally connected to trigger 104. A pin 126 pivotally connects proximal linkage 122 and distal linkage 124 to trigger 104. Pin 126 is also slidably disposed within opposed arcuate channels or slots 102c formed in opposed handle half-sections 102a, 102b. In this manner, as trigger 104 is actuated, pin 126 rides along opposed arcuate channels 102c (see FIGS. 3-5E), and causes opposed proximal coupling portion 122b of proximal linkage 122 and distal coupling portion 124a of distal linkage 124 to separate from one another.

Drive assembly 120 further includes a push rod 132 having a distal end 132a and a proximal end 132b and supported within a push rod channel 132c defined in housing 102. Push rod 132 is configured to translate longitudinally within push rod channel 132c and engage a toggle 134. Toggle 134 is spring loaded with a bias for clockwise rotation (or rotation in a first direction) about a pivot point 134a. As will be discussed in further detail below, as trigger 104 is actuated, proximal linkage 122 exerts a force on push rod 132 driving push rod 132 in a proximal direction. Push rod 132 in turn exerts a force on toggle 134 causing toggle 134 to rotate counter-clockwise (e.g., in a second direction opposite the first direction) about pivot point 134a. As shown in FIGS. 3-5E, push rod 132 includes a length "A." It is contemplated that length "A" of push rod 132 is configured to control the distance that push rod 132 has to travel prior to engaging toggle 134 and may be chosen accordingly.

With continued reference to FIGS. 3-5E, drive assembly 120 includes a clip pusher bar 140 slidably supported within and through housing 102 of handle assembly 100. Clip pusher bar 140 includes a flange 142a supported on a proximal end 140a thereof, and a clip pusher coupling tip (not shown) formed at a distal end 140b thereof. Flange 142a has a diameter "D" such that flange 142a abuts toggle 134 in the starting position. Accordingly, distal translation of clip pusher bar 140 is prevented by toggle 134 when toggle 134 is in the starting position shown in FIG. 3. Clip pusher bar 140 is dimensioned such that when trigger 104 is actuated, clip pusher coupling tip projects from nose 102c of housing 102 of handle assembly 100.

A biasing member 144 (e.g., a compression spring) is interposed between housing 102 of handle assembly 100 and flange 142a of clip pusher bar 140. Biasing member 144 acts on clip pusher bar 140 to bias or urge clip pusher bar 140 in a distal direction. It is contemplated that the clockwise spring bias of toggle 134 produces a greater force than the distal spring bias of biasing member 144. Accordingly, clip pusher bar 140 is unable to translate distally past toggle 134 when trigger 104 is not actuated.

Drive assembly 120 further includes a jaw pusher 146 slidably supported within housing 102 of handle assembly 100. Jaw pusher 146 includes a proximal end 146a pivotally connected to distal coupling portion 124a of distal linkage 124, and a jaw pusher coupling tip 146c formed at a distal end 146b thereof. Jaw pusher 146 defines a lumen 146d therethrough for receipt of and slidable passage of clip pusher bar 140 therein. Jaw pusher 146 is dimensioned such that jaw pusher coupling tip 146c thereof projects from nose 102c of housing 102 of handle assembly 100.

With continued reference to FIGS. 1-4, and with additional specific reference to FIGS. 5A-7, a firing stroke of surgical clip applier 10 is shown and described below. With surgical clip cartridge assembly 300 loaded in endoscopic assembly 200, as trigger 104 of handle assembly 100 is actuated to a fully actuated position, a distal-most clip "C1" of the plurality of surgical clips "C" is loaded into and formed by a pair of jaws 214 of endoscopic assembly 200.

Figure 5A:
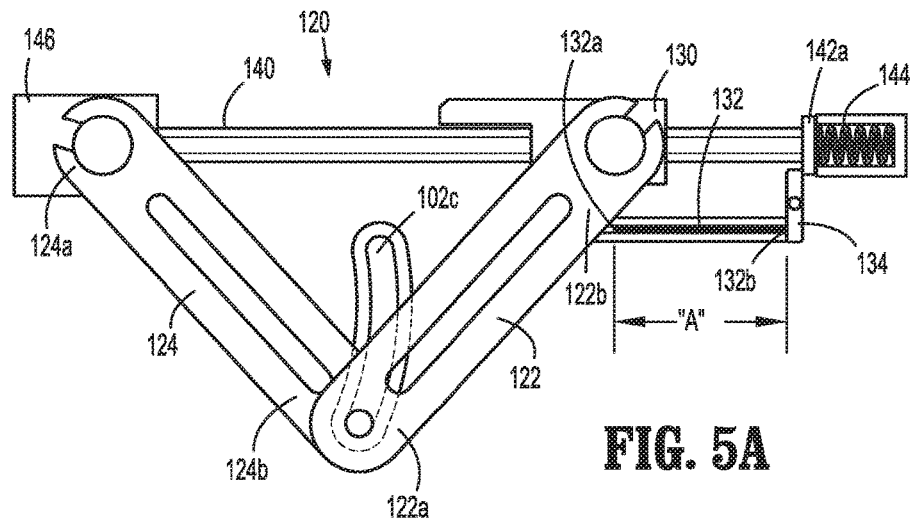
FIGS. 5A-5E are schematic elevational views of the drive assembly illustrated in FIGS. 3 and 4, illustrating an actuation of a trigger of the surgical clip applier.

In particular, FIG. 5A illustrates drive assembly 120 prior to actuation of trigger 104 and FIGS. 5B-5E details the incremental actuation of drive assembly 120 as surgical clip applier 10 is fired. As trigger 104 is actuated in the direction of arrow "E (see FIG. 3)," trigger 104 acts on proximal linkage 122 to move proximal coupling portion 122b of proximal linkage 122 in a proximal direction (as indicated by arrow "F" of FIG. 3), and acts on distal linkage 124 to move distal coupling portion 124a of distal linkage 124 in a distal direction (as indicated by arrow "G" of FIG. 3). Further, distal coupling portion 122a of proximal linkage 122 and proximal coupling portion 124b of distal linkage 124 are moved along opposed arcuate channels 102c in the direction indicated by arrow "H."

Figure 5B:
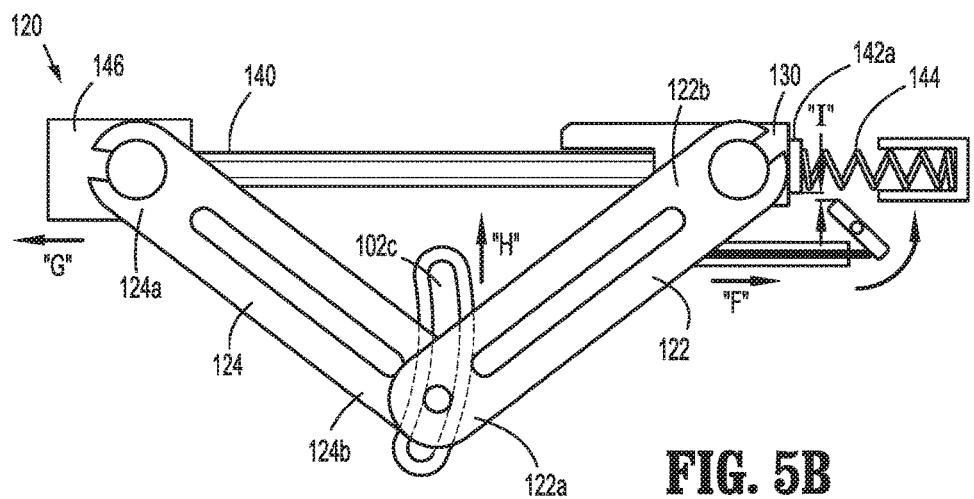

As proximal coupling portion 122b is moved in the direction of arrow "F," proximal linkage 122 engages distal end 132a of push rod 132. In turn, push rod 132 translates along push rod channel 132c to exert a rotation force on toggle 134 in a counter-clock wise (e.g., second) direction. As shown in FIG. 5B, the counter-clock wise rotation of toggle 134 creates a clearance "I" which is sufficient for flange 142a to clear toggle 134 thereby allowing biasing member 144 to expand and drive clip pusher bar 140 distally until flange 142a of clip pusher bar 140 abuts against guide block 130.

As clip pusher bar 140 of handle assembly 100 is moved in a distal direction, clip pusher bar 140 engages endoscopic assembly 200, which in turn, acts on cartridge assembly 300 to load the distal-most surgical clip "C1" into the pair of jaws 214.

Figure 5C:
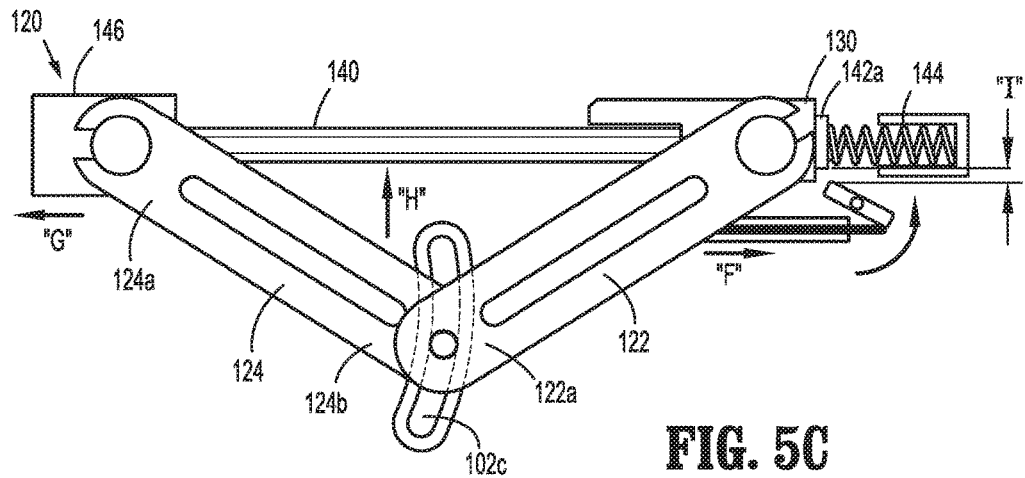
Figure 5D:
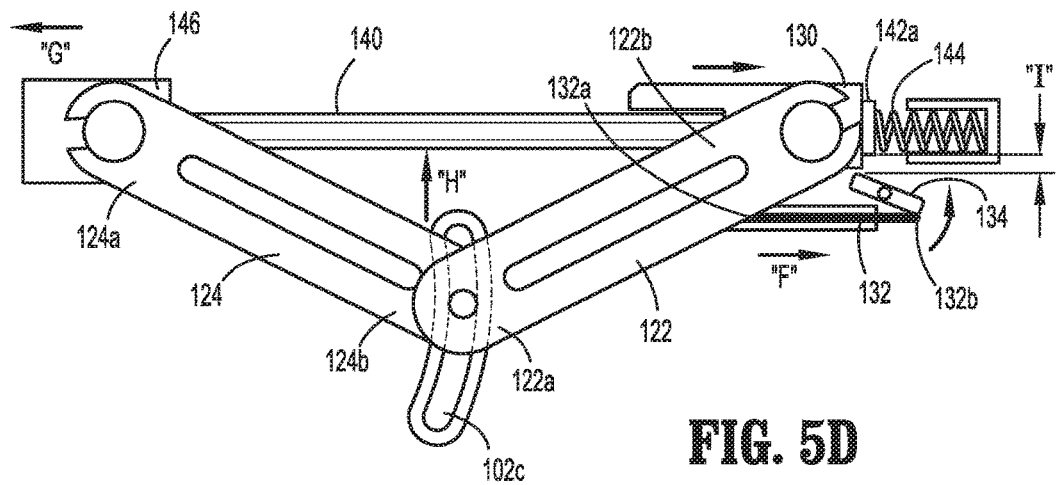

Once flange 142a of clip pusher bar 140 is abutting guide block 130 and as trigger 104 is actuated further in the direction given by arrow "E," proximal linkage 122 continues to move guide block 130 in a proximal direction, and guide block 130 acts on flange 142a of clip pusher bar 140 to urge clip pusher bar 140 in a proximal direction. Simultaneously, as shown in FIG. 5C, proximal linkage 122 maintains contact with distal end 132a of push rod 132 such that push rod 132 maintains contact with toggle 134. This in turn maintains clearance "I" between toggle 134 and flange 142a such that guide block 130 is able to urge clip pusher bar 140 proximally until flange 142a clears toggle 134 (see FIG. 5D) and is located proximal to toggle 134.

As clip pusher bar 140 is moved in a proximal direction, clip pusher bar 140 engages endoscopic assembly 200, which in turn engages surgical clip cartridge assembly 300 to urge the remaining plurality of surgical clips "C" in a proximal direction. Surgical clip cartridge assembly 300 proximally retracts the remaining plurality of surgical clips "C" until each remaining clip of the plurality of surgical clips "C" is retracted.

As mentioned above, the actuation of trigger 104 in the direction of arrow "E," also acts on distal linkage 124 to move distal coupling portion 124a of distal linkage 124 in a distal direction (as indicated by arrow "G" of FIG. 3). As distal coupling portion 124a of distal linkage 124 is moved in a distal direction, distal coupling portion 124a urges jaw pusher 146 in a distal direction. With jaw pusher 146 connected to endoscopic assembly 200, as jaw pusher 146 is moved in the distal direction indicated by arrow "G," the pair of jaws 214 approximate to the closed position.

Figure 7:
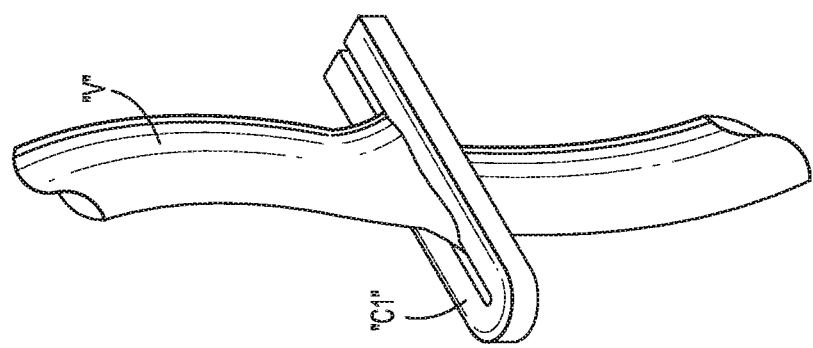
FIG. 7 is a perspective view of a surgical clip formed on a vessel.

With the distal-most surgical clip "C1" loaded in the pair of jaws 214, as the pair of jaws 214 approximate to the closed position, distal-most surgical clip "C1" is formed therebetween, for example, on a vessel "V" or the like, as shown in FIG. 7.

With distal-most surgical clip "C1" formed, trigger 104 may be released and returned to an unactuated position either by or with the assistance of trigger return spring 104a (see FIG. 3). As trigger 104 is returned to an unactuated position, trigger 104 acts on proximal linkage 122 to move guide block 130 in a distal direction, and acts on distal linkage 124 to move jaw pusher 146 in a proximal direction.

Figure 5E:
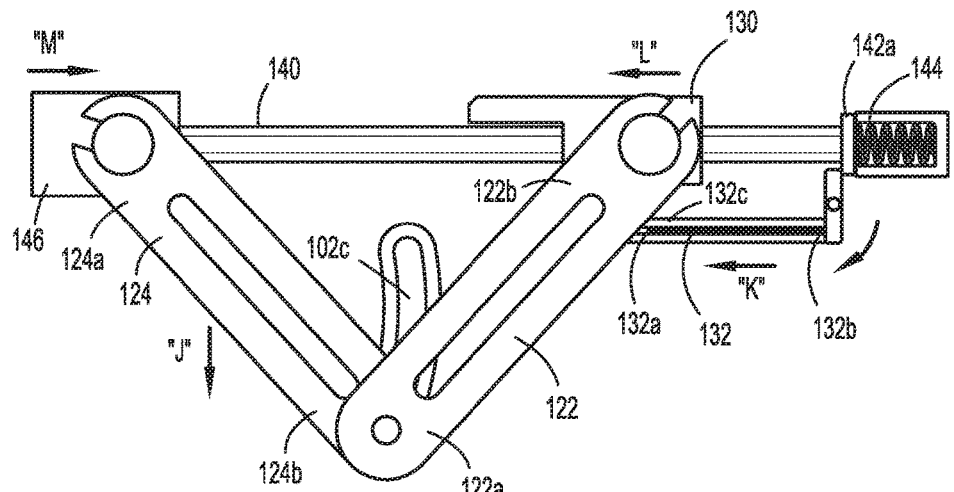

In particular, as shown in FIG. 5E, when trigger 104 is released, distal coupling portion 122a and proximal coupling portion 124b move along opposed arcuate channels 102c in the direction indicated by arrow "J." Simultaneously, proximal coupling portion 122b moves distally in the direction indicated by arrow "L" and distal coupling portion 124a moves proximally in the direction indicated by arrow "M." As distal coupling portion 122a moves in the direction indicated by arrow "J" and proximal coupling portion 122b moves in the direction indicated by arrow "L," proximal linkage 122 loses contact with distal end 132a of push rod 132. As a result, the bias of toggle 134 rotates toggle 134 clockwise to return toggle 134 to its starting position and exerts a force on push rod 132 in the direction indicated by "K." At this stage, clearance "I" between toggle 134 and flange 142a no longer exists. Accordingly, flange 142a of clip pusher 140 is unable to advance distally past toggle 134, thereby resetting clip applier 10 for another firing.

In use, surgical clip applier 10, as mentioned above, is capable of loading different surgical clip cartridge assemblies 300 in endoscopic assembly 200. Specifically, endoscopic assembly 200 may be loaded with a surgical clip cartridge assembly 300 that is loaded with the plurality of surgical clips "C" having a first size, or endoscopic assembly 200 may be loaded with a surgical clip cartridge assembly 300 that is loaded with the plurality of surgical clips "C" having a second size different than the first size.

In this manner, the user or surgeon may load a surgical clip cartridge assembly 300, loaded with a particular size of surgical clips, depending on the particular surgical procedure to be performed. Additionally, during a surgical procedure, if the need arises to use a different sized surgical clip, the user or surgeon may eject or unload the surgical clip cartridge assembly 300 that is loaded in endoscopic assembly 200 and then load a new surgical clip cartridge assembly 300 (having a different sized plurality of surgical clips loaded therein as compared to the unloaded surgical clip cartridge assembly 300) into endoscopic assembly 200.

In accordance with the present disclosure, it is contemplated that surgical clip applier 10 includes a reusable and sterilizable handle assembly 100 that may be used for multiple surgical procedures; a reusable and sterilizable endoscopic assembly 200 that may also be used for multiple surgical procedures; and a disposable, single use clip cartridge assembly 300 (e.g., wherein the clip cartridge assembly 300 is disposed of when unloaded from endoscopic assembly 200). It is contemplated that endoscopic assembly 200 may be disposed of following the particular surgical procedure and not reused or sterilized.

Also in accordance with the present disclosure, it is further contemplated that a surgical kit may be provided including a single handle assembly 100, a single endoscopic assembly 200, and a plurality of clip cartridge assemblies 300 including at least a first set of clip cartridge assemblies loaded with a plurality of surgical clips having a first size and a second set of clip cartridge assemblies loaded with a plurality of surgical clips having a second size different than the first size. The kit may include instructions for the assembly or surgical clip applier 10, the use of surgical clip applier 10, and the processing of surgical clip applier assembly 10 following use.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical clip applier, comprising:
   a handle assembly including:
      a housing;
      a trigger pivotally supported on and extending from the housing; and
      a drive assembly supported within the housing and operatively actuatable by the trigger, the drive assembly including:
         at least one linkage connected to the trigger, the at least one linkage slidably supported in the housing;
         a guide block slidably supported in the housing, the guide block operatively connected to the trigger;
         a clip pusher bar slidably supported in the guide block, the clip pusher bar including a flange at a proximal end thereof and configured for distal translation to advance a surgical clip;

a toggle distal of the flange of the clip pusher bar, the toggle actuatable between a first position and a second position and configured to limit the distal translation of the clip pusher bar when the toggle is in the first position; and a push rod supported in the housing, the push rod engageable by the at least one linkage to actuate the toggle between the first position and the second position; and an endoscopic assembly extending distally from the housing of the handle assembly, the endoscopic assembly including:

a shaft assembly extending from the housing, the shaft assembly including an outer tube; and a pair of jaws supported in and extending from a distal end of the outer tube, wherein when the toggle of the handle assembly is in the second position, the pair of jaws are free to form the surgical clip on tissue.

2. The surgical clip applier according to claim 1, wherein the at least one linkage includes a first end and a second end, the first end of the linkage being pivotably connected to the trigger and the second end of the linkage being pivotably connected to the guide block such that actuation of the trigger translates the guide block proximally.

3. The surgical clip applier according to claim 2, wherein the first end of the at least one linkage and the trigger are slidably coupled to a slot defined in the housing such that upon actuation of the trigger, the first end of the at least one linkage rides along the slot.

4. The surgical clip applier according to claim 3, wherein as the first end of the at least one linkage rides along the slot, the at least one linkage exerts a force on the push rod such that the push rod translates proximally to exert a force on the toggle to actuate the toggle from the first position to the second position.

5. The surgical clip applier according to claim 1, wherein the toggle is spring loaded and includes a bias such that the toggle abuts the flange in the first position.

6. The surgical clip applier according to claim 5, wherein the drive assembly further includes a biasing member acting on the clip pusher bar to urge the clip pusher bar in a distal direction.

7. The surgical clip applier according to claim 6, wherein a force exerted by the bias of the toggle is greater than a force exerted by the biasing member acting on the clip pusher bar such that the biasing member is unable to push the flange past the toggle when the toggle is in the first position.

8. The surgical clip applier according to claim 7, wherein in the second position, the biasing member acts on the clip pusher bar to urge the clip pusher bar distally until the flange thereof abuts the guide block.

9. The surgical clip applier according to claim 7, wherein when the trigger is actuated, the at least one linkage simultaneously engages the push rod and the guide block such that the toggle is in the second position and the guide block drives the abutting flange proximally past the toggle.

10. The surgical clip applier according to claim 1, wherein in the second position, there is a clearance between the toggle and the flange such that the clip pusher bar is able to translate distally to locate the flange distal to the toggle.

11. The surgical clip applier according to claim 1, wherein the drive assembly further includes a trigger return spring acting on the trigger to urge the trigger to an unactuated position.

12. A surgical clip applier, comprising:
a handle assembly including:
a housing;
a trigger pivotally supported on and extending from the housing; and
a drive assembly supported within the housing and operatively actuatable by the trigger, the drive assembly including:
a distal linkage slidably supported in the housing, the distal linkage including a first end and a second end, the second end of the distal linkage connected to the trigger;
a proximal linkage slidably supported in the housing, the proximal linkage including a first end and a second end, the first end of the proximal linkage connected to the trigger;
a jaw pusher slidably supported in the housing, the jaw pusher operatively connected to the trigger;
a guide block slidably supported in the housing, the guide block operatively connected to the trigger;
a clip pusher bar including a flange at a proximal end thereof and configured for distal translation to advance a surgical clip;
a toggle distal of the flange of the clip pusher bar, the toggle actuatable between a first position and a second position and configured to limit the distal translation of the clip pusher bar when the toggle is in the first position; and
a push rod supported in the housing, the push rod engageable by at least one of the proximal linkage and the distal linkage to actuate the toggle between the first position and the second position; and an endoscopic assembly extending distally from the housing of the handle assembly, the endoscopic assembly including:
a shaft assembly extending from the housing, the shaft assembly including an outer tube; and
a pair of jaws supported in and extending from a distal end of the outer tube, wherein when the toggle of the handle assembly is in the second position, the pair of jaws are free to form a surgical clip on tissue.

13. The surgical clip applier according to claim 12, wherein the distal linkage, the proximal linkage, and the trigger are slidably coupled to a slot defined in the housing such that upon actuation of the trigger, the distal linkage, the proximal linkage, and the trigger ride along a channel defined within the slot.

14. The surgical clip applier according to claim 12, wherein actuation of the trigger translates the jaw pusher distally and translates the guide block proximally.

15. The surgical clip applier according to claim 12, wherein as the proximal linkage rides along the slot, the proximal linkage exerts a force on the push rod such that the push rod translates proximally to exert a force on the toggle to actuate the toggle from the first position to the second position.

16. The surgical clip applier according to claim 12, wherein the toggle is spring loaded and includes a bias such that the toggle abuts the flange in the first position.

17. The surgical clip applier according to claim 16, wherein the drive assembly further includes a biasing member acting on the clip pusher bar to urge the clip pusher bar in a distal direction.

18. The surgical clip applier according to claim 17, wherein a force exerted by the bias of the toggle is greater than a force exerted by the biasing member acting on the clip pusher bar such that the biasing member is unable to push the flange past the toggle when the toggle is in the first position.

19. The surgical clip applier according to claim 17, wherein in the second position, the biasing member acts on the clip pusher bar to urge the clip pusher bar distally until the flange thereof abuts the guide block.

20. The surgical clip applier according to claim 19, wherein when the trigger is actuated, the proximal linkage simultaneously engages the push rod and the guide block such that the toggle is in the second position and the guide block drives the abutting flange proximally past the toggle.

21. The surgical clip applier according to claim 12, wherein in the second position, there is a clearance between the toggle and the flange such that the clip pusher bar is able to translate distally to locate the flange distal to the toggle.

22. The surgical clip applier according to claim 12, wherein the drive assembly further includes a trigger return spring acting on the trigger to urge the trigger to an unactuated position.

* * * * *